(12) United States Patent
Liesi

(10) Patent No.: US 7,741,436 B2
(45) Date of Patent: Jun. 22, 2010

(54) BIOLOGICALLY ACTIVE PEPTIDES AND THEIR USE FOR REPAIRING INJURED NERVES

(76) Inventor: Päivi Liesi, Tilkankatu 2 B 25, FI-00300 Helsinki (FI)

( * ) Notice: Subject to any disclaimer, the term of this patent is extended or adjusted under 35 U.S.C. 154(b) by 0 days.

(21) Appl. No.: 12/141,129

(22) Filed: Jun. 18, 2008

(65) Prior Publication Data

US 2008/0249021 A1  Oct. 9, 2008

Related U.S. Application Data

(62) Division of application No. 10/492,850, filed as application No. PCT/FI02/00831 on Oct. 25, 2002, now abandoned.

(30) Foreign Application Priority Data

Oct. 26, 2001  (FI)  ................................. 20012082

(51) Int. Cl.
 *A61K 38/06*  (2006.01)
 *A61K 49/00*  (2006.01)
(52) U.S. Cl. ....................... 530/331; 424/9.1
(58) Field of Classification Search ................ None
 See application file for complete search history.

(56) References Cited

U.S. PATENT DOCUMENTS

| | | | |
|---|---|---|---|
| 3,590,722 A | 7/1971 | Leptrone | |
| 3,645,756 A | 2/1972 | Huth et al. | |
| 5,780,090 A | 7/1998 | Frerot et al. | |
| 2002/0168718 A1 | 11/2002 | Hubbell et al. | |

FOREIGN PATENT DOCUMENTS

| | | |
|---|---|---|
| DE | 20010297 U1 | 10/2000 |
| EP | 0 067 425 B1 | 12/1982 |
| GB | 2 284 422 A | 6/1995 |
| WO | WO-93/24155 A1 | 12/1993 |
| WO | WO-9324155 A1 | 12/1993 |
| WO | WO-94/04560 A1 | 3/1994 |
| WO | WO-98/43686 A1 | 10/1998 |
| WO | WO-98/45325 A1 | 10/1998 |
| WO | WO-9843686 A1 | 10/1998 |
| WO | WO-99/00418 A1 | 1/1999 |
| WO | WO-9900418 A1 | 1/1999 |
| WO | WO-01/66164 A1 | 9/2001 |

OTHER PUBLICATIONS

Guo et al., PNAS, 101(25):9205-9210, 2004.*
Kasai et al., Biochemistry, 46:3966-3974, 2007.*
Fahy et al. Anesthesiol Clin North America, 20(2):441-462, 2002.*
Liesi, Paivi et al., Journal of Neuroscience Research, vol. 66, 2001, pp. 1047-1053.
Liesi, Paivi et al., FEBS Lett., vol. 224, No. 1, 1989, pp. 141-148.
T. Serafini et al., Cell. 1994, Aug. 12: 78(3) :409-24; PubMed Abstract ID:8062384.
P. Liesi et al., Journal of Neuroscience Research, 40:199-206 (1995).
M. Matsuzawa et al., Int. J. Devl. Neuroscience, vol. 14, No. 3, pp. 283-295, 1996.
M. Matsuzawa et al., Journal of Neuroscience Research, 53:114-124 (1998).
J. Meyerhardt et al., Cell Growth & Differentiation, vol. 10, 35-42, Jan. 1999.
Eric Guadango et al., GLIA 47: pp. 138-149 (2004)..
Ron Liebkind et al., Journal of Neuroscience Research 73: pp. 637-643 (2003).
P. Liesi, Experientia 46 (1990).
Paivi Liesi et al., Journal of Neuroscience Research 64: pp. 144-167 (2001).
Paivi Liesi et al., Journal of Neuroscrence Research 66: pp. 1047-1053 (2001).
Paivi Liesi et al., Experiemental Neurology 173: pp. 31-45 (2002).
S. Murtomaki et al., Jburnal of Neuroscience Research 32: pp. 261-273 (1992).
Hiroshi Nishimune et al., Nature Publishing Group vol. 432, pp. 580-587, Dec. 2, 2004.
Edouard Palu et al., Journal of Neuroscience Research 69: 243-256 (2002).
Arja Pasternack et al., The Journal of Biological Chemistry, vol. 277, No. 51, pp. 49662-49667, Dec. 20, 2002.
Markus Wiksten et al., Journal of Neuroscience Research 71: pp. 338-352 (2003).
Markus Wiksten et al. Journal of Neuroscience Research 78: pp. 403-410 (2004).
Markus Wiksten et al. Journal of Neuroscience Research 78: pp. 411-419 2004.
Milman et al. (1980). Acta Derma Venerol. 60, 85-87.
Carney (2005). Drug. Discovery Today 10, 1268.
Nagaratnam et al. (2002). Journal of Clinical Neuroscience. 9, 473-476.
Hanafiah et al. (1989) Journal of the Royal Society of Medicine. 84, 48-49.
Miura et al. (2000). Experiemental Neurology. 166, 115-126.
Kawamata et al. (1997). PNAS. 94, 8179-8184.
Rogeji et al. (1989) JCB, 109, 823-.
Mercadante et al. (1998). Journal of Pain and Symptoms Management. 16, 317-322.
Hoyte et al. (2004). Current Molecular. Medicine. 4,131-136.
Sun et al. (1993) Neuroreport. 4, 1147-1150.

* cited by examiner

*Primary Examiner*—John D. Ulm
*Assistant Examiner*—Stacey MacFarlane
(74) *Attorney, Agent, or Firm*—Birch, Stewart, Kolasch & Birch, LLP

(57) ABSTRACT

The present invention relates to biologically active peptides derived from the neurite outgrowth-promoting domain of laminin-1, i.e. the γ1-chain of laminin-1. These peptides include the decapeptide RDIAEIIKDI (SEQ ID NO: 1) and the truncated peptides derived therefrom comprising the biologically active domain thereof, the tripeptide KDI. The invention is directed to the biologically active tripeptide motif KDI, and to its use in promoting regeneration of neuronal or non-neuronal tissues and, in specific, to its use in the treatment of spinal cord injuries.

3 Claims, 12 Drawing Sheets

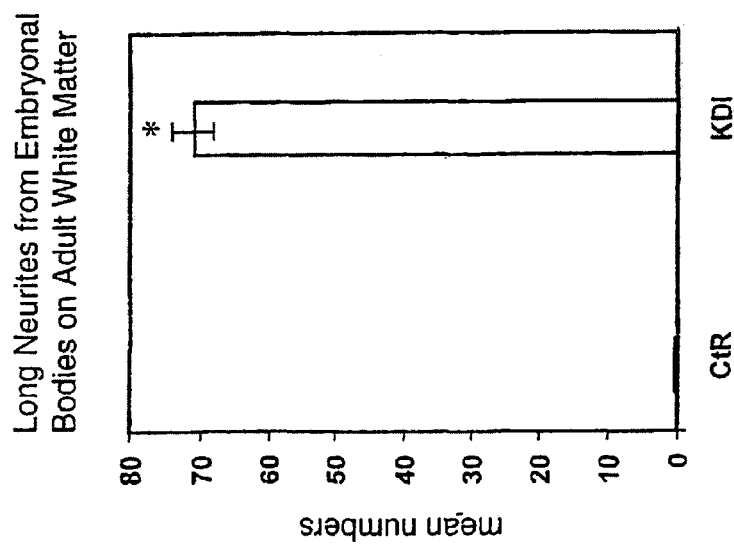

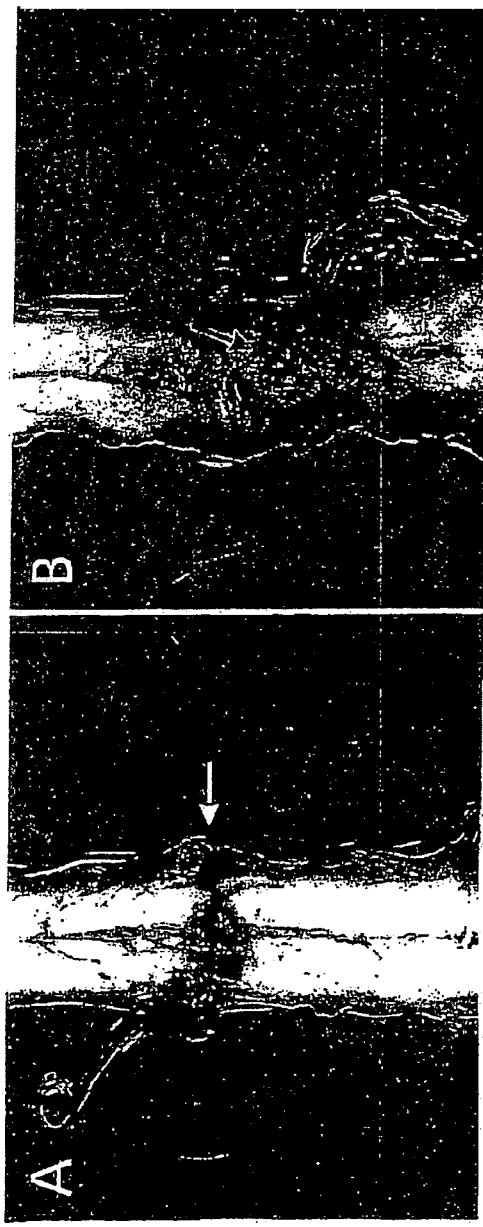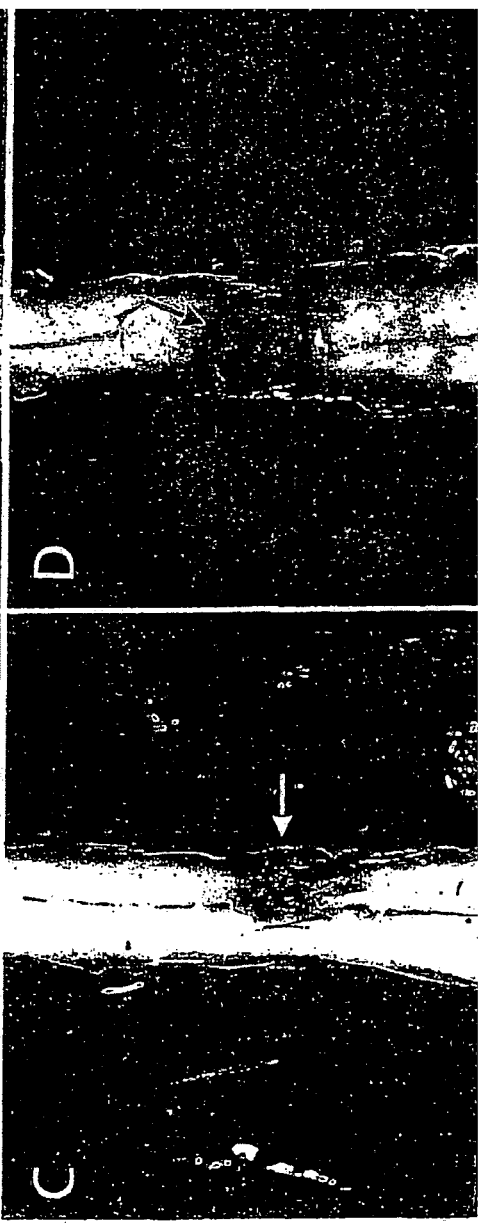

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      decapeptide derived from the neurite outgrowth-promoting domain of
      laminin-1

<400> SEQUENCE: 1

Arg Asp Ile Ala Glu Ile Ile Lys Asp Ile
1               5                   10

<210> SEQ ID NO 2
<211> LENGTH: 6
<212> TYPE: PRT
```

```
-continued

<213> ORGANISM: Artificial Sequence
<220> FEATURE:
<223> OTHER INFORMATION: Description of Artificial Sequence:  Synthetic
      peptide derived from the neurite outgrowth-promoting domain of
      laminin-1

<400> SEQUENCE: 2

Glu Ile Ile Lys Asp Ile
1               5

<210> SEQ ID NO 3
<211> LENGTH: 49
<212> TYPE: PRT
<213> ORGANISM: artificial sequence
<220> FEATURE:
<223> OTHER INFORMATION: Description of Artificial Sequence:  Synthetic
      peptide derived from the neurite outgrowth-promoting domain of
      laminin-1

<400> SEQUENCE: 3

Ser Asp Leu Asp Arg Lys Val Ser Asp Ala Ala Ile Met Asp Tyr Asn
1               5                   10                  15

Arg Asp Ile Ala Glu Ile Ile Lys Asp Ile His Asn Leu Glu Asp Ile
            20                  25                  30

Lys Lys Thr Leu Pro Thr Gly Cys Phe Asn Thr Pro Ser Ile Glu Lys
        35                  40                  45

Pro
```

BIOLOGICALLY ACTIVE PEPTIDES AND THEIR USE FOR REPAIRING INJURED NERVES

This application is a Divisional of application Ser. No. 10/492,850 filed Apr. 16, 2004, now abandoned and for which priority is claimed under 35 U.S.C. §120; and application Ser. No. 10/492,850 is the national phase of PCT/FI02/00831 filed Oct. 25, 2002 which claims priority under 35 U.S.C. §119 of Finnish Application No. 20012082 filed in Finland on Oct. 26, 2001. The entire contents of all of the above applications are hereby incorporated by reference.

FIELD OF THE INVENTION

The present invention relates to biologically active peptides derived from the neurite outgrowth-promoting domain of laminin-1, i.e. the γ1-chain of laminin-1. These peptides include the decapeptide RDIAEIIKDI (SEQ ID NO: 1) and the truncated peptides derived therefrom comprising the biologically active domain thereof, the tripeptide KDI. The invention is directed to the biologically active tripeptide motif KDI, and to its use in promoting regeneration of neuronal or non-neuronal tissues and, in specific, to its use in the treatment of spinal cord injuries.

BACKGROUND OF THE INVENTION

Laminin-1 promotes neurite outgrowth of both central and peripheral neurons of the rodent (Liesi, 1990). One of the neurite outgrowth domains of laminin-1 has been mapped to the C-terminal decapeptide RDIAEIIKDI (SEQ ID NO: 1) (P1543; p20; Liesi et al., 1989) of the γ1-chain of laminin-1.

Both human brain and spinal cord neurons attach and respond by neurite outgrowth to mouse laminin-1. Sequence analysis of the human brain isoforms of laminin-1 show approximately 96-100% homology to the mouse prototype (Liesi et al., 2001).

In recent years, multiple and diverse functions of laminin-1 have been reported in neural tissues. For example, laminin-1 has been shown to prevent neurotoxicity of the amyloid-β-peptide involved in neuronal death of Alzheimer disease (Bronfman et al., 1996; Drouet et al., 1999). Laminin-1 further affects development of dendritic spines of the cerebellar Purkinje cells (Seil, 1998), and influences memory processing by modulation of LTP (Nakagami et al., 2000). As most of the members of the laminin-superfamily are also present in neurons and glial cells of the human embryonic CNS (Liesi et al., 2001), laminins may have specific and diverse effects on development and mature function of the human CNS.

Using specific γ1 laminin antibodies on cultures of central neurons, the neurite outgrowth domain of the γ1-chain of laminin-1 has been shown to play a major role in neuronal migration and axon guidance. The nuclear rotation phase of cerebellar neuronal migration (Liesi et al., 1995), neuronal differentiation (Matsuzawa et al., 1996a), and axon guidance of rat hippocampal neurons (Matsuzawa et al., 1998) have all been shown to be influenced by the neurite outgrowth domain of the γ1-chain of laminin-1. In previous studies, we have shown that the neurite outgrowth domain of the γ1-chain of laminin-1 accumulates in brains of Alzheimer disease patients (Murtomäki et al., 1992) as well as in the weaver mouse cerebellum (Murtomäki et al., 1995). Therefore we have proposed that an increased accumulation of high concentrations of the neurite outgrowth domain of the γ1-laminin may be toxic to neurons. In line with this hypothesis, antibodies against the neurite outgrowth domain that neutralize the γ1-chain peptides restore both cell survival and neurite outgrowth of the weaver granule neurons (Liesi and Wright, 1996).

WO publication 93/24155 discloses a medical device, useful as a graft in repairing injured nerve tissues, specifically peripheral nerves, the device containing the decapeptide P1543. WO publication 98/43686 discloses fibrin-based, biocompatible materials for, for instance, peripheral nerve regeneration. The materials contain various bioactive peptides, including the above-indicated decapeptide. Furthermore, Hager et al. (1998) showed that the corresponding peptide derived from mouse laminin-1 modulates the electrical activity the neurons of rat neocortex.

WO publication 94/04560, on the other hand, discloses protein factors having Schwann cell mitogenic activity. The peptide sequences disclosed in the application include a sequence comprising the KDI motif. Use of the factors for e.g. neural regeneration is suggested.

U.S. Pat. No. 5,780,090 discloses flavoring ingredients for food products, comprising tripeptides having hydrophobic amino acid residues. Preparation of the tripeptide KDI is described in the patent, but no medical use is suggested for the peptide.

Recently, netrin-1 has been shown to act on central neurons via a G-protein coupled receptor mechanism (Corset et al., 2000). Interestingly, the KDI-sequence is present in the chicken netrin-1 (Serafini et al., 1994), and the human netrin-protein (Meyerhardt et al., 1999) also has this domain, although modified. It is unclear, however, if the presence of this short sequence has any functional significance in these proteins. The KDI-sequence may be hidden in netrins either by conformation or glycosylation of the proteins.

SUMMARY OF THE INVENTION

While investigating the mechanisms of action of the neurite outgrowth decapeptide (RDIAEIIKDI; P1543) of the γ1-chain of laminin-1 on primary cerebellar neurons, we identified a tripeptide (KDI) sequence responsible for the biological functions, i.e. attachment and neurite outgrowth, of this decapeptide (RDIAEIIKDI (SEQ ID NO: 1); P1543). We found that both the P1543 and the tripeptide KDI promoted attachment and neurite outgrowth of human embryonic CNS neurons. These peptides also induced electrical currents in rat cerebellar neurons. The tripeptide motif KDI, however, turned out to have superior characteristics in treating spinal cord injuries.

Consequently, one object of the invention is the use of the decapeptide RDIAEIIKDI (SEQ ID NO: 1) or a truncated peptide derived therefrom comprising the tripeptide motif KDI in the manufacture of a medicament for use in a method for treating spinal cord injuries.

As a result of our new finding that the peptide motif KDI is responsible for the biological activity of the neurite outgrowth promoting domain of laminin-1, one object of the present invention is a truncated peptide derived from the decapeptide RDIAEIIKDI (SEQ ID NO: 1) including the biologically active peptide motif KDI for use as a medicament. A specific object of the invention is the tripeptide KDI for use as a medicament.

A primary object of this invention is a biologically active tripeptide motif KDI for use in a method for treating spinal cord injuries.

Due to the neurite outgrowth promoting activity of the KDI peptide, said peptide can also be used in a method of repairing injured nerves in general. Consequently, a further object of this invention is the tripeptide KDI for use in a method for treating injured nerves, e.g. peripheral nerves.

A still further object of the invention is a method for repairing injured nerves in an animal in need of such repairing, said method comprising administering to said animal an efficacious amount of a biologically active peptide comprising the tripeptide motif KDI. The most preferable is the tripeptide KDI.

Another object of the invention is a method for the treatment of spinal cord injuries in an animal in need of such treatment, said method comprising administering to said animal an efficacious amount of a biologically active peptide comprising the tripeptide motif KDI. Preferable peptides are the decapeptide RDIAEIIKDI (SEQ ID NO: 1) and the truncated peptides derived therefrom comprising the tripeptide motif KDI. The most preferable for the purposes of the invention is the tripeptide KDI.

In view of the finding that the peptide motif KDI is a biologically active peptide, we suggest that any peptide comprising the tripeptide motif KDI may be useful in regeneration and renewal of damaged or degenerating tissues, either neuronal or non-neuronal. A peptide with the KDI-motif could be used in these functions in both soluble and substrate-bound forms.

Therefore, a still further object of the invention is a pharmaceutical composition, which comprises as an active ingredient the tripeptide motif KDI, in association with at least one pharmaceutically acceptable carrier and/or diluent.

BRIEF DESCRIPTION OF THE DRAWINGS

FIG. 8 Effect of the KDI peptide on the number of long neurites; extending from embryonal bodies onto white matter of the adult human spinal cord. KDI=KDI tripeptide added; CtR=control, no peptide added.

FIG. 10A to 10D Stereomicroscopic images of placebo-treated (10A and 10B) and KDI peptide-treated (10C and 10D) spinal cords of adult rats three months after injury. In A and C, the ventral spinal cord is photographed. In B and D, the dorsal pole is shown. The connective tissue scar at the dorsal pole is present in both placebo and KDI-treated spinal cords, but the scar is considerably smaller in the KDI-treated case (D).

DETAILED DESCRIPTION OF THE INVENTION

Figure 1:
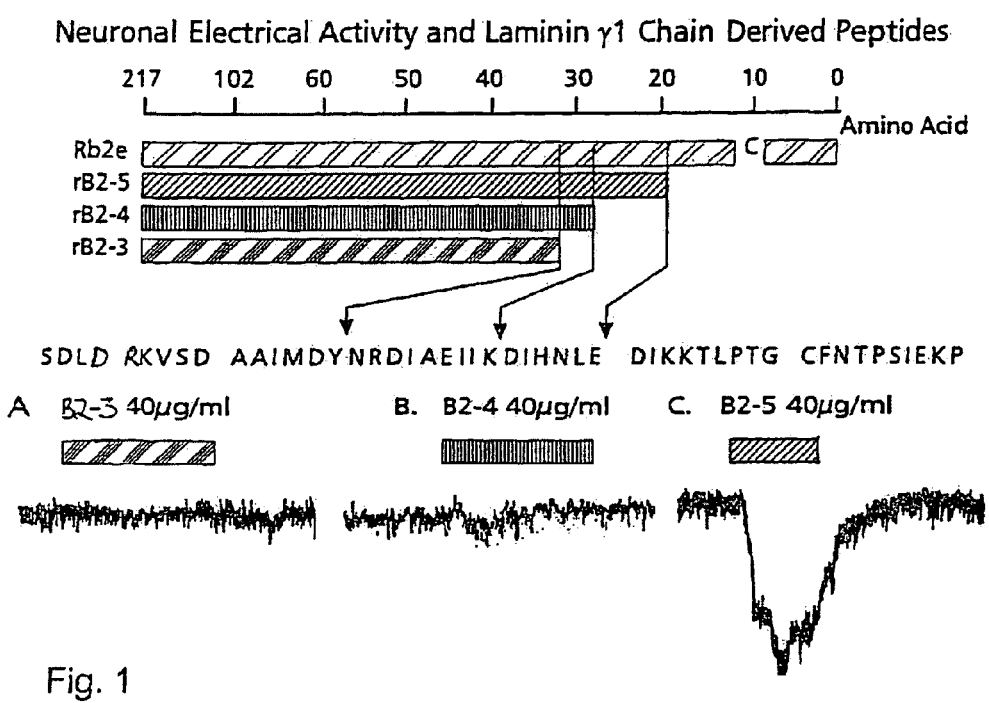
FIG. 1 The effects of fusion proteins containing the P1543 peptide sequence (SEQ ID NO: 3) on electrical properties of cerebellar granule neurons on a laminin-1 substratum.

The present invention provides biologically active peptides for medical use. The peptides are useful in soluble or substrate-bound forms in repairing injured nerves, for instance peripheral nerves, or injured or degenerating central nervous system. The peptides are particularly useful for the treatment of spinal cord injuries.

Using an experimental model of human CNS injury, we show that survival and neurite outgrowth of human central neurons is significantly enhanced by the soluble KDI-domain of γ1 laminin. To test the ability of the biologically active KDI-domain to protect human central neurons from environmental factors, we used two different culture systems. First, we plated freshly isolated neurons from the human embryonic spinal cord and neocortex on monolayers of injured astrocytes of the human spinal cord. Second, we plated "embryonal bodies" containing the stem cells of the human CNS on white matter of the cryostat sections of the adult human spinal cord.

On human spinal cord astrocytes, neurons plated at low density showed poor neurite outgrowth that was significantly improved by the presence of nanomolar concentrations of the KDI-domain in the culture medium. Viability of the neurons was also significantly enhanced by low concentrations of the KDI peptide. On cross-sections of the adult human spinal cord, neurons in the embryonal bodies of the human CNS cells refused to come out and their neurofilament-positive neurites circled within the borders of the embryonal bodies. In the presence of the KDI-domain, neurons extended long neurites out of the embryonal bodies. The neurites attached and extended on the white matter directly in contact with cross-sectioned myelin sheets of the adult human spinal cord. In the absence of the KDI-domain, the neurites never extended on myelin but always grew on top of the glial cells that spread on the spinal cord myelin during a prolonged time in vitro.

Our data indicate that human central neurons are viable and extend long neurites in spite of the inhibitory signals of their environment, if the KDI-domain of the γ1 laminin is applied at suitable concentrations. Both myelin-derived and glia-derived factors that hamper neuronal regeneration are significantly neutralized and central neurons extend long fibres, and are more viable than without the protective KDI-domain. This data strongly imply that the KDI-domain may neutralize the axon growth inhibitory signals of the adult mammalian CNS, and justify further experiments to test the ability of the KDI-domain to promote regeneration in vivo.

In our in vivo experiments on spinal cord injuries of adult male rats we made complete lumbar spinal cord transections. The animals were divided into a test group and a control group, to which KDI peptide and a placebo were administered, respectively. The animals underwent weekly tests of their motor functions during a period of three months. After 3 months, the animals in each group were euthanized and the spinal cords were examined. The results of the motoric tests show a significant difference between the KDI group and the placebo group. The mean motor scores for the rats of the KDI group, and the stereomicroscopic images of their spinal cords show that the recovery of the spinal cord was unquestionable.

We thus propose that the KDI-domain may enhance regeneration of injuries in the adult mammalian CNS. As this peptide also enhanced viability of human CNS neurons regardless the brain region, we propose that this sequence could be used to prevent neuronal degeneration and death in neurodegenerative diseases. In a clinically applicable method to promote regeneration of spinal cord injuries in humans the KDI peptide could be applied either in soluble form or attached to biodegradable polymers, that slowly release the peptide and simultaneously provide a direction for the growing axons. The re-growth of axons would be monitored during a period of 3 months by testing of the motor function of the operated animals. After 3 months the tissues would be collected and subjected to histological, molecular biological and immunohistochemical analysis to verify the effects of the tripeptide and the extent of regeneration. The extent of axon growth through the injured area could then be monitored using DiI-labelling of the nerve fibres.

The KDI peptide could also be used in treating neurodegenerative diseases, such as Parkinson's or Alzheimer's disease. A suitable pharmaceutical composition for that purpose is an injectable liquid to be administered to the intrathecal space or injected to the brain tissue.

The peptides of the present invention may be prepared using conventional methods for peptide synthesis, as described, for instance, by Liesi et al. (1989).

Pharmaceutical compositions containing the peptides of the invention for the treatment of spinal cord injuries are preferably liquid preparations suitable for injection. The peptides may be dissolved in sterile saline or water. A pharmaceutical composition may include a modification of the KDI peptide that allows its direct access to the CNS through the blood-brain-barrier, and also include biodegradable polymers, which slowly release the peptide and simultaneously, as an additional advantage, provide a direction for the growing axons.

The peptides of the present invention may thus be administered in an efficacious amount within a wide dosage range. The efficacious amount depends on the age and condition of the tissue in question. Peptides of the present invention may be administered either as a single dose, or as continuous administration using, for instance, a mini pump system. In the latter case, the daily dosage will not exceed the dose of a single injection, and must be predetermined by animal experimentation.

The concentrations of a peptide of the invention in a pharmaceutical composition are generally between 0.01 and 100 μg/ml. However, it should be noted that the optimal concentration of the KDI peptide may be domain dependent or tissue dependent, and therefore pre-testing of the dosage is of utmost importance. Determining of the suitable dosage for individual treatments is within the skills of those familiar with the art.

When treating other nerve injuries, such as injuries of peripheral nerves, a useful pharmaceutical preparation containing the KDI peptide motif can be prepared and administered, for example, as described for the P1543 decapeptide in WO 93/24155.

The pharmaceutical composition of the present invention can be administered by any means that achieve the intended purpose. For instance, for the treatment of spinal cord injuries the composition can be administered to the injury site via a catheter. A most preferable way of administration is using a mini pump system to administer the peptide composition directly to the trauma area of the spinal cord. This can be easily carried out in connection with orthopaedic surgery for disclosing the trauma area.

The pharmaceutical compositions of the present invention can be administered to any animal that can experience the beneficial effects of the peptides of the invention. Human beings are foremost among such animals, although the invention is not intended to be limited to the medical treatment of human beings.

Previous studies have shown that the neurite outgrowth domain of the γ1 laminin has a dual neurotrophic/neurotoxic function on central neurons, but it remains to be seen, if the KDI-motif, present in both mouse and human γ1 laminin, is a general neurotoxicity/neurotrophicity motif for central neurons or whether it is active only in the neurite outgrowth domain of they γ1 laminin.

The dual function of the domain in question should also be taken into account while determining the suitable dosage range of the peptides of the invention.

The data obtained in the present studies indicate that γ1 laminin and its individual domains may modulate neuronal function by altering their electrical properties. We show that the tripeptide domain KDI is the biologically active domain of the neurite outgrowth decapeptide (P1543) of the γ1 laminin. An advantageous feature of the KDI peptide is the fact that it is a short peptide, being not immunogenic, and therefore risks for immunological reactions are minimal. Furthermore, as the peptide has previously been disclosed as a flavoring ingredient, it should be safe for human use.

We also show that the KDI-domain acts on primary cultures of CNS neurons via a G-protein coupled receptor mechanism and induces potassium currents in central neurons. These are novel concepts not previously demonstrated for any laminin, and imply an additional role for the γ1-chain of laminin-1 in mature function of the brain.

Experimental

Materials and Methods

Human CNS Tissues

Human fetal CNS tissues were obtained from 6-12 week old fetuses after legal abortion and after informed consent from the patients. The tissues were collected by the permission of the Ethics Committee of the Helsinki University Central Hospital. The CNS tissues, identified under a stereomicroscope, were first placed in cold saline and processed for tissue culture experiments. Normal adult spinal cord tissues were from the Neurological Specimen Bank (Baltimore, USA).

Isolation and Culturing of Human Embryonic Spinal Cord Glial Cells

The CNS tissues were first placed in cold saline. The spinal cord tissues were identified under a stereomicroscope, and carefully freed of meninges. To obtain monolayer cultures of human spinal cord glial cells, the cells were dissociated by mechanical trituration using a Pasteur-pipette, and placed in Petri dishes (Corning, N.Y., USA) containing 10% fetal calf serum (Hyclone, Logan, UH) in DMEM-F12 (Gibco, U.K.) supplemented with penicillin and streptomycin as described (Liesi et al. 2001). In this manner, cultures with 100% TUJ1-positive glial cells were obtained, which indicated that the glial cells were precursors of astrocytes.

Human Neuronal Cultures on Synthetic Peptides

The cells were dissociated by trituration in a sterile culture medium (RPMI 1640) containing penicillin (100 U/ml), streptomycin (100 μg/ml) and 200 μM L-glutamine. The dissociated cells were plated on glass coverslips pre-coated (Liesi et al., 1989) with mouse laminin-1 (Boehringer-Mannheim, Germany) or with the peptides KDI-gc and RDIAEIIKDI-gc (SEQ ID NO: 1), as described elsewhere (Matsuzawa et al., 1996b). The peptides were from the Multiple Peptide Systems (La Jolla, Calif.). The cultures were maintained for 24 hrs, fixed in 2% paraformaldehyde, and processed for immunocytochemistry.

Immunocytochemistry of Human Neuronal Cultures

Immunocytochemistry for neuron specific tubulin isoform TUJ1 was performed as described elsewhere (Liesi et al., 2001). In short, the cells were permeabilized in methanol for 5 min at −20° C., washed in PBS and incubated with monoclonal TUJ1-antibodies for 1 hr at room temperature. The antibody was of high specificity and was used at 1:500 dilution. After immunocytochemistry, the coverslips were mounted in PBS:glycerol (1:1) and viewed with Olympus Provis fluorescence microscope with appropriate filter combinations.

Rat Cerebellar Cultures

Sixteen-day pregnant Sprague-Dawley female rats were obtained from Taconic Farms, and maintained at the animal facility of National Institute of Alcohol Abuse and Alcoholism (NTH), fed with NTH-31 diet, containing 20,000 IU/kg vitamin A after autoclaving. The rats were allowed to give birth, and cerebellar tissues of 3-day-old female pups were aseptically isolated as described previously (Matsuzawa et al., 1996a). A suspension of single cells was obtained by trypsinizing the cerebella as described elsewhere (Liesi and Wright, 1996), after which $10^5$ cells were plated on 22 mm glass coverslip pre-coated with laminin-1. The cells were incubated in an atmosphere of 95% air/5% $CO_2$ at +37° C. in RPMI 1640 culture medium supplemented with penicillin and streptomycin and 200 μM L-glutamine. After 24 hrs, the cells were used for electrophysiology.

Electrophysiology

Recordings were done at room temperature using a List EPC-7 patch-clamp amplifier in voltage-clamped whole-cell patch configuration as described previously (Liesi and Wright, 1996). Pipettes were pulled from borosilicate glass and lightly fire polished. Experiments were performed at room temperature. Whole-cell currents were recorded on a Gould 2400S strip chart recorder. Cell membrane potential was clamped at −40 mV unless otherwise noted. All bath solutions were applied through pinch-valves that controlled the flow from multiple reservoirs to a single 200 μm ID barrel of fused silica. Standard bath solution was RPMI 1640, buffered with 10 mM HEPES (pH 7.4). The standard pipette solution contained (in mM): $CsMeSO_4$ 100, CsCl 15, BAPTA 5, HEPES 10 (pH KOH-adjusted to 7.2). Tests for reversal potentials were conducted in low $K^+$ bath solution containing (in mM): NaCl 150, KCl 5, $CaCl_2$ 1, HEPES 10 (pH adjusted to 7.2 with NaOH) and a high $K^+$ bath solution, containing (in mM): NaCl 115, KCl 40, $CaCl_2$ 1, HEPES 10 (pH adjusted to 7.2 with NaOH). All bath solutions contained 300 nM TTX. The pipette solution for reversal potential trails was (in mM): K-aspartate 110, NaCl 10, $MgCl_2$ 2, BAPTA 5, HEPES 10 (pH NaOH adjusted to 7.2). Nernst reversal potentials were calculated according to Hille (1992). Peptides and fusion proteins were added to aliquots of the standard bath solution immediately before the trials. Between recordings, the dish was perfused with standard bath solution (RPMI 1640, buffered with 10 mM HEPES, pH 7.4). System quality checks were conducted by switching between two reservoirs each containing standard bath solution to detect perfusion artifacts and determine if any active peptides had adhered in the tubing. The peptides RDIAEIIKDI (SEQ ID NO: 1), EIIKDI (SEQ ED NO: 2), and KDI were all from Multiple Peptide Systems (San Diego, Calif.). The fusion proteins (B2-3; B2-4; B2-5) and α1 laminin control peptides (AG10; AJ5; AI12) were from Drs. Yoshi Yamada and Atsusi Utani (National Institute of Dental Research, NIH) and were purified as described (Utani et al., 1994; Nomizu et al., 1995).

Survival of Human Embryonic Neocortical Neurons on Glial Cells of the Human Spinal Cord Human embryonic spinal cord glial cells were cultured till confluency in 10% fetal bovine serum as described (Liesi et al., 2001). The confluent cultures were trypsinized and cells replated at 100 000 cells/22 mm glass coverslip, and grown till confluency. The confluent cultures were changed into normal adult human serum, and injured by using a 18 G gauge sterile needle. The KDI peptide was added at 1 μg/ml (3 μM) and at 10 μg/ml (30 μM) concentration and the P1543 peptide (p20) was added at a concentration of 1 μM, and 50-100 000 freshly isolated human embryonic neocortical neurons were added on the glial cells. The control cultures had neurons added either without the peptide or the lesion. The cells were cultured for 72 hrs in 5% $CO_2$/95% air at +37° C., and fixed for quantitation of neurons and measurement of their neuritic lengths. The neurons on glial monolayers were visualized by immunostaining using mouse monoclonal antibodies against a neuron-specific tubulin isoform (TUJ1). The results were evaluated by counting neurons in six random fields on 3 different coverslip per experiment. In this way, more than 300 neurons were counted per experiment. Statistical analysis of the results was performed using one-way analysis of Varians (ANOVA) and Student-Newman-Keuls multiple comparisons test on the Instat (v2.03) program (GraphPad, San Diego, Calif.).

Survival of Human Embryonic Spinal Cord Neurons on Glial Cells of the Human Spinal Cord Freshly isolated tissue from the human embryonic spinal cord (8-10 weeks of age) was mechanically dissociated and cells were plated at 50,000 on a 22 mm glass coverslip confluent with human embryonic spinal cord glia. The glial monolayers were injured using a 18 G needle prior to plating of the neurons. The cells were cultured in normal adult human serum for 72 hrs. The numbers of spinal cord neurons on the glial monolayers in the presence or absence of KDI (0.0355 µg/ml-1.0 µg/ml) was estimated on TUJ1-labelled cultures. The statistical analysis was performed using one-way-variance analysis (ANOVA), and the Student-Newman-Keuls multiple comparisons test.

Embryonal Bodies of Human CNS-Regions

Embryonal bodies containing immature stem cells from spinal cord, or neocortex were obtained by placing the mechanically dissociated CNS-cells on 10 cm Petri dishes (Corning) in Neurobasal medium (Gibco, U.K.) with B27-supplement (Gibco, U.K.), antibiotics and 500 µM L-glutamine. The embryonal bodies failed to attach onto the plastic and grew in aggregates that also increased in size and released new embryonal bodies into the culture medium.

Experimental Model System (I) of Human Spinal Cord Injury: Glial Influence

Confluent cultures of the spinal cord glial cells were trypsinized using Trypsin-EDTA, and cells replated at a density of $5 \times 10^4$ on a 22 mm glass coverslip. The cells were cultivated until they formed confluent monolayers. At this point, their culture medium was changed into 10% normal adult human serum in DMEM-F12, and glial monolayers were injured using 18 G-needle. After injury, the KDI peptide (Multiple Peptide Systems, La Jolla, Calif., USA) was added into the culture medium after which a suspension of freshly dissociated cells from spinal cord or neocortex was added at $2 \times 10^4$ on one coverslip. After 24-48 hrs, the cultures were fixed in 2% paraformaldehyde in PBS, pH 7.4 for 15 min and immunostained for TUJ1 as described previously (Liesi et al., 2001).

Viability and neurite outgrowth of human CNS-neurons on the spinal cord glial cells were evaluated by counting 10 random fields of cells in 6 different cultures. A total of 265 cells were counted. The numbers of long neurites (>10 cell soma) were estimated similarly. One-way-variance analysis (ANOVA) was used to evaluate the results.

Experimental Model System (II) of Human Spinal Cord Injury: Myelin Influence

Cryostat sections (10 µm) of adult normal human spinal cord were cut in coronal plain on SuperFrost Plus slides (Menzel, Germany). Each slide had three sections. The slides with freshly cut sections were immediately placed in sterile Quadriperm-plates (In Vitro Systems & Services, Germany) and 10 ml of culture medium was added. The culture medium was 1.0% normal adult human serum in DMEM-F12 supplemented with penicillin and streptomycin. Two embryonal bodies were placed on areas of white matter on top of each section, and the cultures were placed in the incubator with 5% $CO_2$/95% air at 98% humidity at +37° C. The KDI peptide (Multiple Peptide Systems, La Jolla, Calif.) was added in the medium at 1-10 µg/ml, and the 10-amino acid precursor (RDIAEIIKDI (SEQ ID NO: 1)) was added at equimolar concentrations. The control cultures received no peptide. After 10 days, the cultures were fixed and immunostained for neurofilament proteins and additional neuronal and glial markers to identify the neurites and cells within the embryonal bodies. Numbers of embryonal bodies attached, and extending neurites directly on the adult white matter tissue were counted on each slide and the results analyzed using one-way-variance-analysis (ANOVA). Numbers of long neurites (>100 µm) extending from embryonal bodies in control cultures and in cultures with 5-10 µg/ml of the KDI peptide in the culture medium were counted and a non-parametric Whitney-Mann test was used to analyze those results.

Studies on Spinal Cord Injuries of Adult Male Rats

Methods and Experimental Design:

Complete transections of the lumbar spinal cord under deep pentobarbiturate anesthesia were made to 40 adult male Sprague-Dawley rats. Osmotic mini pumps were implanted subcutaneously to allow continuous flow of the KDI peptide (KDI-group) used at pre-tested concentrations (10-100 µg/ml) or a placebo (placebo-group). Morphine was given to both of the groups to alleviate the postoperative pain. The animals underwent weekly tests of their motor function during a period of three months. The motor score testing was carried out using a standard set of tests of motor evaluation (walking, tow-spread, placing and withdrawal). The mini pumps initially provided the drugs for 30 days, and when feasible, additional experiments were carried out with prolonged (up to 3 months) application. After 3 months, the animals in each group were euthanized and spinal cords were either deep frozen for immunocytochemistry, biochemistry and RNA-work, or fixed in 4% paraformaldehyde for in situ hybridization and histological analysis of recovery. DiI-injections of the fixed spinal cord well above the injury site were used to monitor the growth of axons across the injury site. The brains and sciatic nerves of the animals were also either deep frozen or fixed and stored for later analysis.

Results

Electrophysiological Effects of Laminin-1-Derived Peptides

Figure 2:
FIG. 2A to 2D The effects of different shorter peptides derived from the P1543 decapeptide on electrical properties of cerebellar granule neurons on a laminin-1 substratum.

Synthetic peptides and fusion proteins from the γ1-chain of laminin-1 were tested for their electrophysiological effects on rat cerebellar neurons (FIG. 1 and FIG. 2).

A fusion protein (B2-5; Utani et al., 1994) covering the P1543 region was able to induce currents (Block C in FIG. 1) similar to those induced by the decapeptide P1543. Application of 40 µg/ml of a fusion protein (B2-3) with a 15 amino acid deletion that cuts off the entire RDIAEIIKDI (SEQ ID NO: 1)-sequence failed to induce a current in cerebellar granule neurons (Block A in FIG. 1). A fusion protein (B2-4) that cuts off the DI-end of the active sequence also failed to induce a current in cerebellar neurons (Block B in FIG. 1).

These results helped us to define even smaller peptides that might identify the actual neurite outgrowth domain, e.g., the smallest biologically active sequence of the γ1-chain of laminin-1.

The 6-amino acid peptide EIIKDI (SEQ ID NO: 2) induced currents in cerebellar granule neurons (FIG. 2A) that were comparable to those induced by P1543 (See FIG. 2D). The shortest peptide that induced currents in central neurons was the tripeptide KDI (FIG. 2B), whereas the unrelated peptides derived from the α1-chain of laminin-1 (AG10; AI12; AJ5) failed to induce currents in the cerebellar granule neurons (FIG. 2C).

Figure 3:
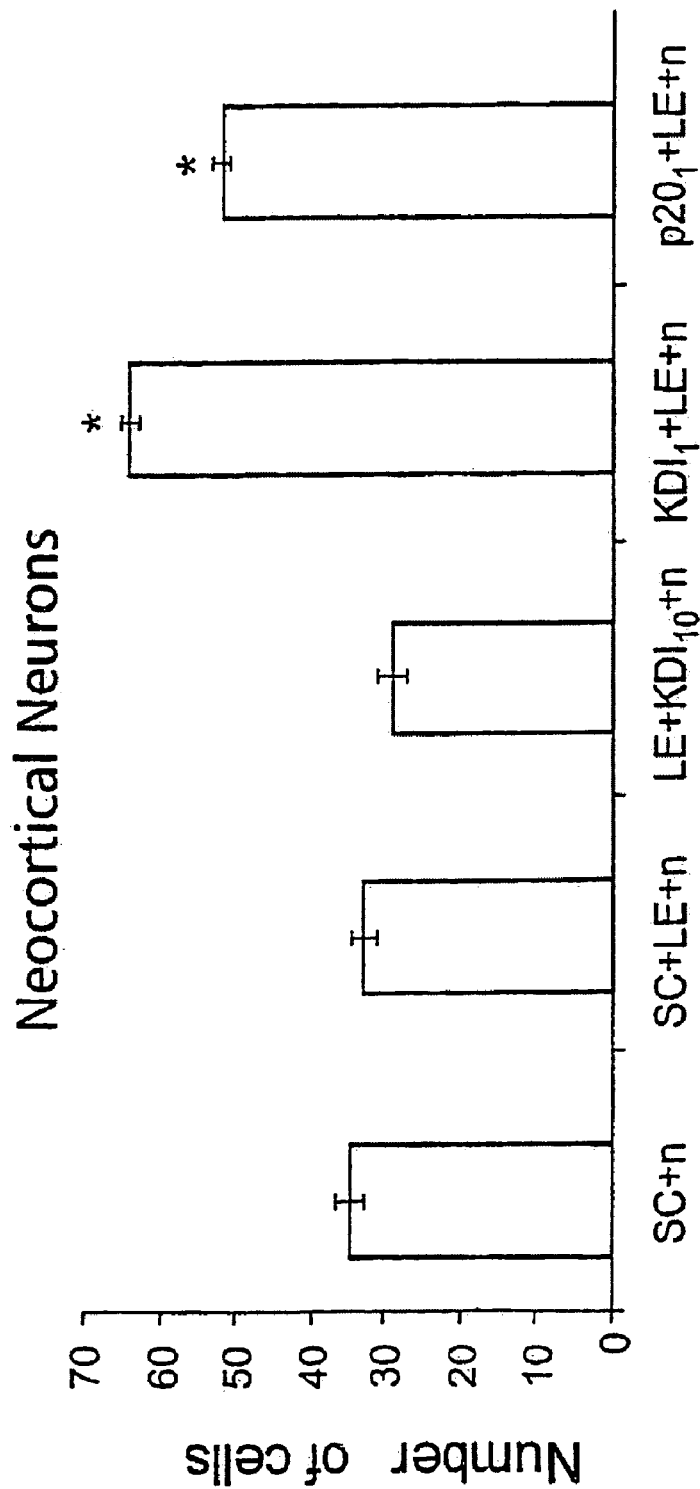
FIG. 3 Mean numbers of viable human embryonic neocortical neurons on glial cells of the human spinal cord 72 hrs after an injury in the presence or absence of soluble KDI peptide at 1 μg/ml or at 10 μg/ml or of the P1543-decapeptide at 1 μg/ml. Abbreviations: (SC+n)=spinal cord glial cells, (SC+LE+n)=lesioned spinal cord glial cells, (LE+KDI$_{10}$+n)= lesioned cells in the presence of 10 μg/ml of the KDI peptide, (KDI$_1$+LE+n)=lesioned cells in the presence of 10 μg/ml of the KDI peptide, (p20$_1$+LE+n)=lesioned cells in the presence of 1 μg/ml of the P1543 peptide.

Survival of Human Embryonic Neocortical Neurons on Glial Cells of the Human Spinal Cord Some neocortical neurons attached and extended neurites on spinal cord glial cells (SC+n), on lesioned spinal cord glial cells (SC+LE+n) or on spinal cord glial cells in the presence of 10 µg/ml of the KDI peptide (LE+$KDI_{10}$+n) (FIG. 3). However, there was no statistical difference of neuronal survival between the different conditions. Addition of 1 µg/ml of the P1543 peptide (p20) caused a significant ($p<0.001$) improvement in the attachment and neurite outgrowth of the neocortical neurons ($p20_1$+LE+n). However, addition of the KDI peptide at 1 µg/ml again significantly ($p<0.001$) improved both attachment and neurite outgrowth of the neocortical neurons ($KDI_1$+LE+n). The improvement caused by KDI (1 µg/ml) was statistically significant as compared to that induced by p20 (1 µg/ml). *p<0.001 in Student-Newman-Keuls multiple comparisons (ANOVA) test.

The results thus indicate that KDI peptide promotes survival of human neocortical neurons on injured spinal cord glial cells. The results also indicate that the KDI peptide is, in low concentrations, better than P1543-peptide in this function.

Figure 4A:
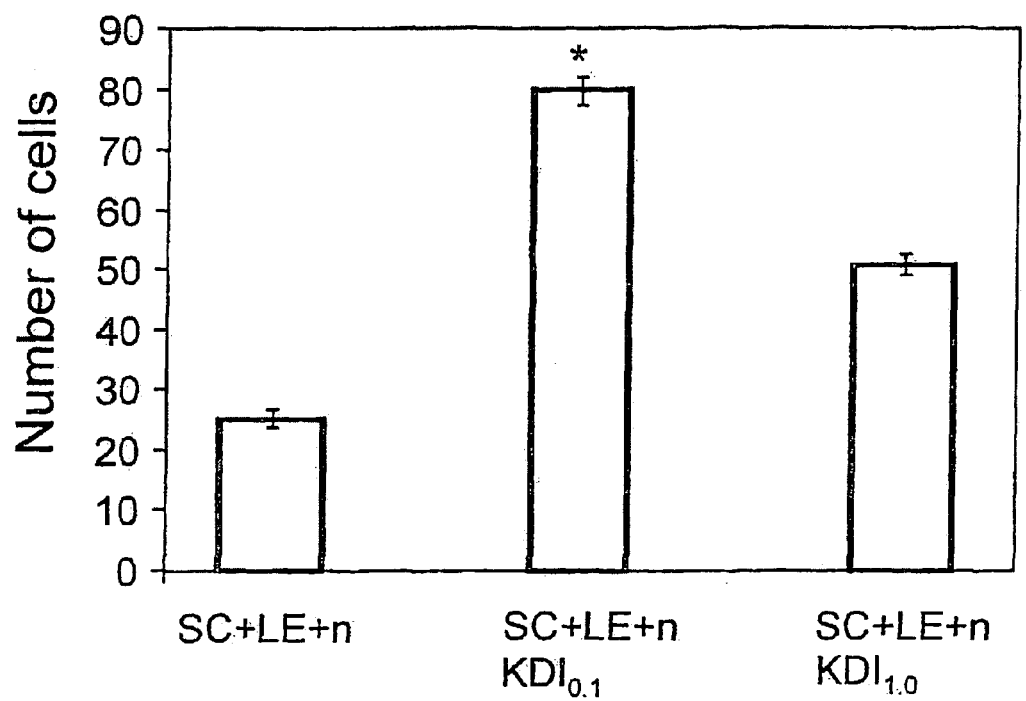
FIG. 4A Numbers of human spinal cord neurons extending long neurites (>100 μm) on monolayers of human spinal cord glial cells after 72 h in vitro. Abbreviations: (SC+LE+n)= lesioned spinal cord glial cells, (SC+LE+n, KDI$_{1.0}$)=lesioned spinal cord glial cells in the presence of 0.1 μg/ml of the KDI peptide, (SC+LE+n, KDI$_{1.0}$)=lesioned spinal cord glial cells in the presence of 1.0 μg/ml of the KDI peptide.

Survival and Neurite Outgrowth of Human Embryonic Spinal Cord Neurons on Glial Cells of the Human Spinal Cord FIG. 4A shows numbers of human spinal cord neurons extending long neurites (>100 µm) on monolayers of human spinal cord glial cells after 72 hrs in vitro. In the absence of KDI peptide, few neurons with long neurites were seen (SC+LE+n). Addition of 0.1 µg/ml of the KDI peptide significantly increased the numbers of long neurites (p<0.001). Note that this concentration was also the best to support survival of the spinal cord neurons. Addition of 1.0 µg/ml of the KDI peptide also significantly increased the numbers of long neurites as compared to the lesion-control.

Figure 4B:
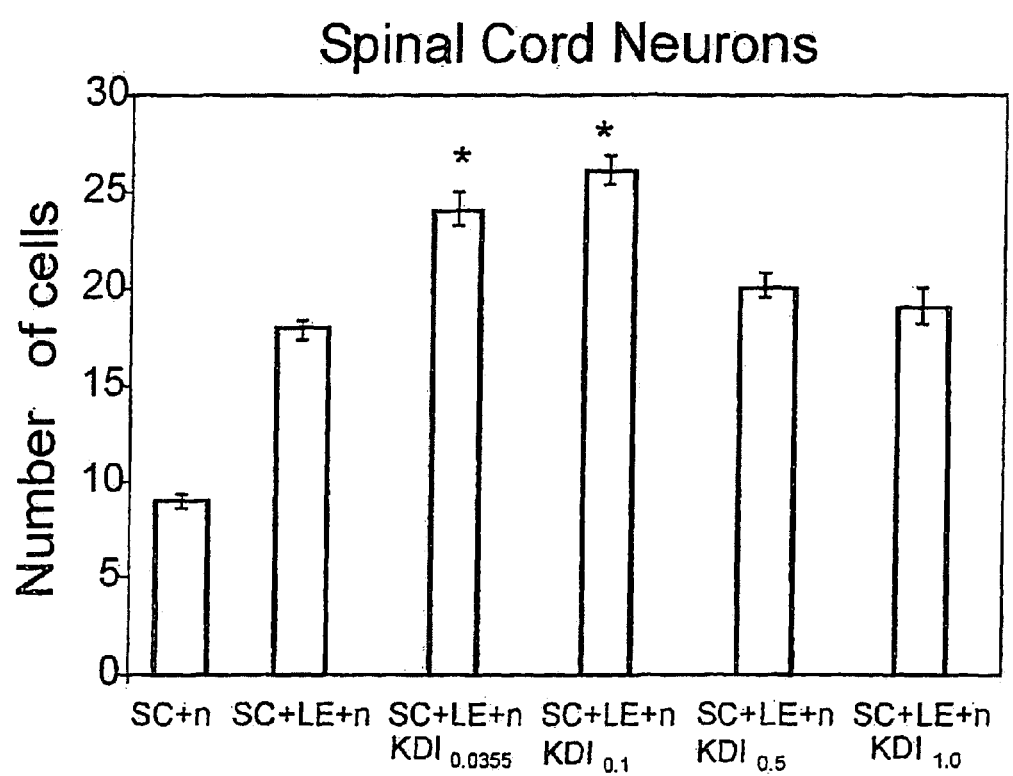
FIG. 4B Numbers of human spinal cord neurons on monolayers of human spinal cord glial cells after 72 h in vitro. Abbreviations: (SC+n)=spinal cord glial cells, (SC+LE+n)= lesioned spinal cord glial cells, (SC+LE+n, KDI$_{0.0355}$– KDI$_{1.0}$)=lesioned spinal cord glial cells in the presence of 0.0355 μg/ml to 1.0 μg/ml of the KDI peptide.

FIG. 4B shows numbers of human spinal cord neurons on monolayers of human spinal cord glial cells after 72 hrs in vitro. In control cultures (SC+n) some spinal cord neurons attached on the glial monolayers, and lesioning of the glial monolayers (SC+LE+n) increased the attachment. Addition of nanomolar concentrations of the KDI peptide (SC+LE+n/KDI0.0355 µg/ml; SC+LE+n/KDI0.1 µg/ml) significantly (p<0.001) enhanced survival of spinal cord neurons. Addition of 0.5 µg/ml or 1.0 µg/ml of the KDI peptide did not promote survival of the spinal cord neurons any better than the lesion by itself (non-significant).

Consequently, FIGS. 4A and 4B show that the KDI peptide is both a survival and neurite outgrowth factor for human spinal cord neurons. Comparison of these data to the results given in FIG. 3 also show that the spinal cord neurons are more sensitive to the dose of KDI than neocortical neurons in this treatment.

Attachment and Neurite Outgrowth of Human Embryonic CNS Neurons

Figure 5A:
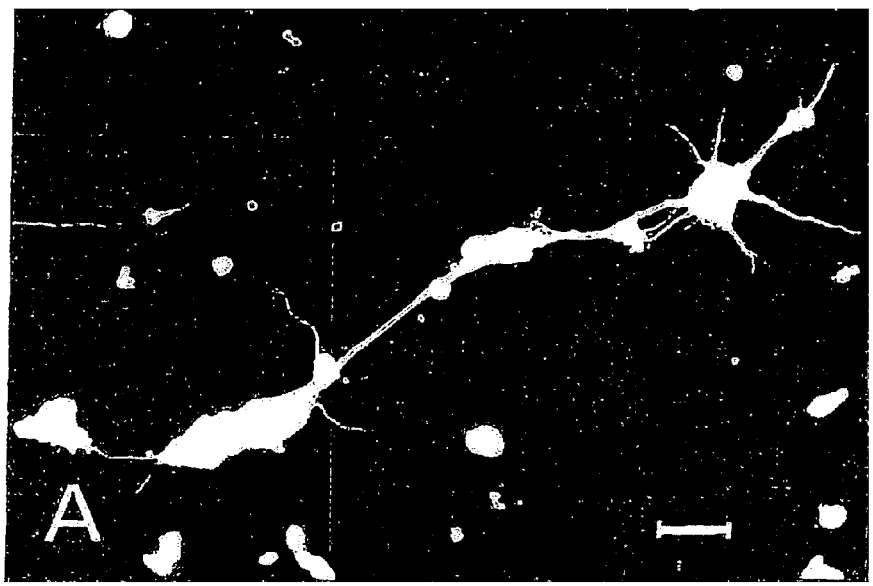
FIG. 5A to 5D Attachment and neurite outgrowth of TUJ1-positive human embryonic brain neurons on peptides KDI-gc (5A-5C) and P1543-gc (5D). Note that "gc" indicates Gly-Cys-addition to allow covalent coupling of the short peptides onto glass as described elsewhere (Matsuzawa et al., 1996b).
Figure 5B:
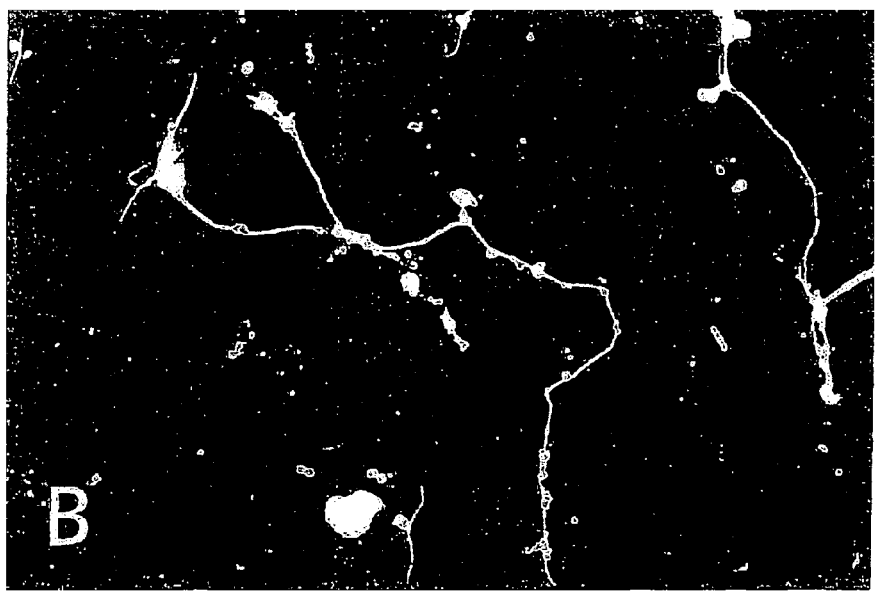
Figure 5C:
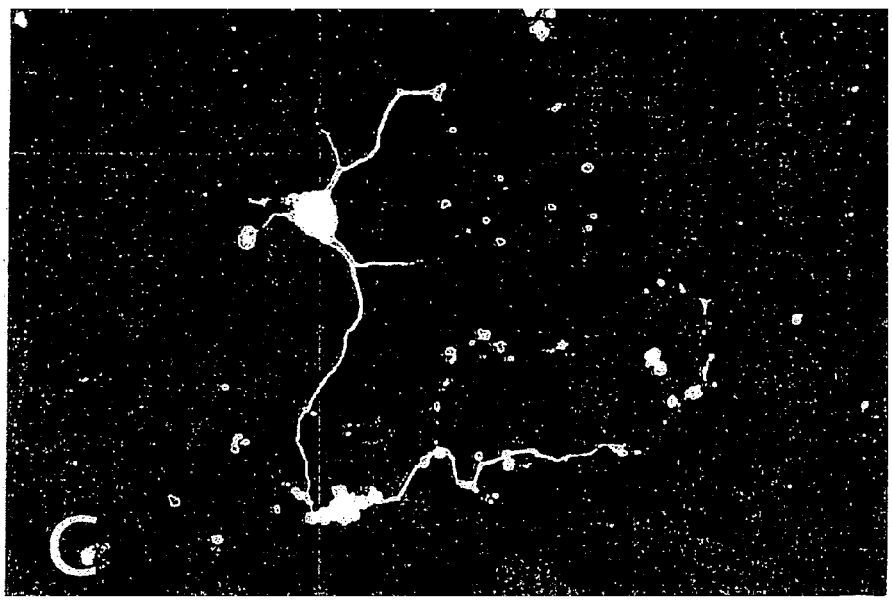
Figure 5D:
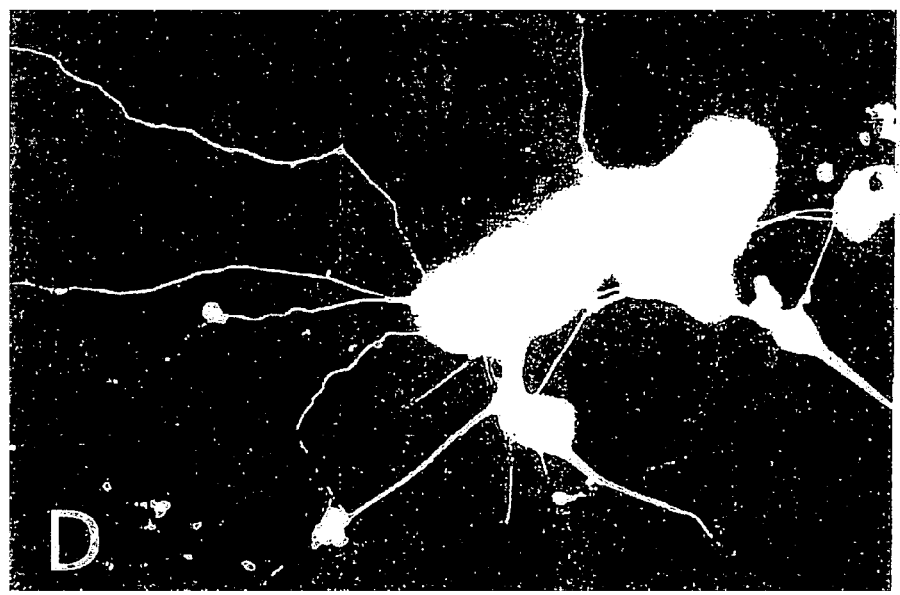

The KDI tripeptide (0.1-10 µg/ml) and the decapeptide P1543 (1 µg/ml; RDIAEIIKDI (SEQ ID NO: 1)) supported attachment and neurite outgrowth of human CNS neurons. The KDI peptide (0.1 µg/ml) covalently cross-linked to glass promotes attachment and neurite outgrowth of human central neurons (FIG. 5A). Two examples of neurite outgrowth of human central neurons on the KDI peptide (10 µg/ml) indicate that neurons attach and extend long neurites on the tripeptide (FIGS. 5B and 5C). P1543 (1 µg/ml) coupled to glass promotes neurite outgrowth of human central neurons as well as the KDI peptide (FIG. 5D). Scale bar=10 µm. No differences were observed in attachment and neurite outgrowth properties of the neurons on these two substrata (not shown).

Figures 6A, 6B:
FIGS. 6A and 6B TUJ1-immunoreactive neurons from the human embryonic spinal cord on top of the injured monolayers of the human spinal cord glial cells after 48 hrs in vitro. 6A: 0.1 μg/ml of the KDI peptide added into the culture medium; 6B: No KDI peptide present in the culture medium.

FIGS. 6A and 6B show TUJ1-immunoreactive neurons from the human embryonic spinal cord on top of the injured monolayers of the human spinal cord glial cells after 48 hrs in vitro. In 6A, a neuron in the lower right corner of the photograph extends a long neurite in the presence of 0.1 µg/ml of the KDI peptide in the culture medium. In 6B, a spinal cord neuron fails to extend long neurites when no KDI peptide is present in the culture medium.

Attachment and Neurite Outgrowth of Embryonal Bodies

Figure 7:
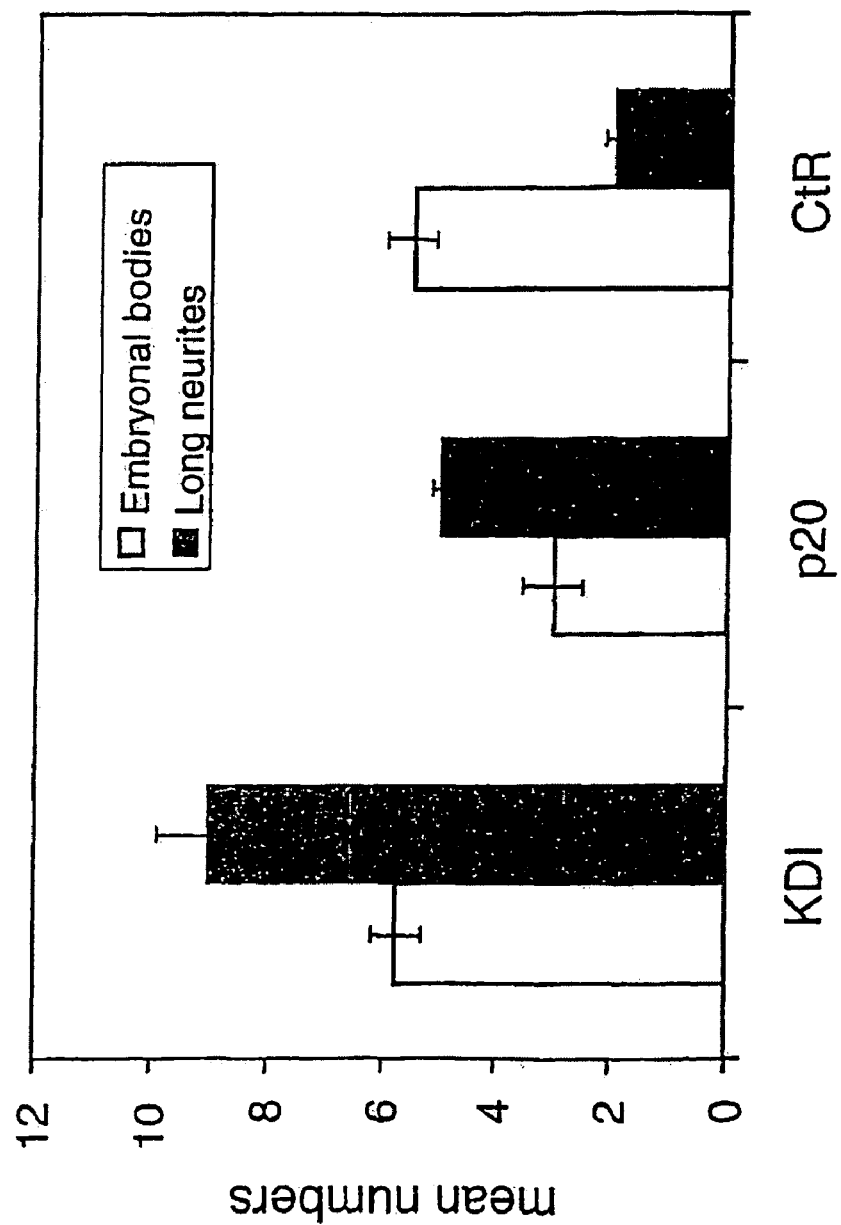
FIG. 7 Mean numbers of embryonal bodies (EBS; open columns) and EBS extending long neurites (black columns) on white matter of cryostat sections of the adult human spinal cord. KDI=KDI tripeptide added; p20=decapeptide P1543 added; CtR=control, no peptide added.
Figure 9A:
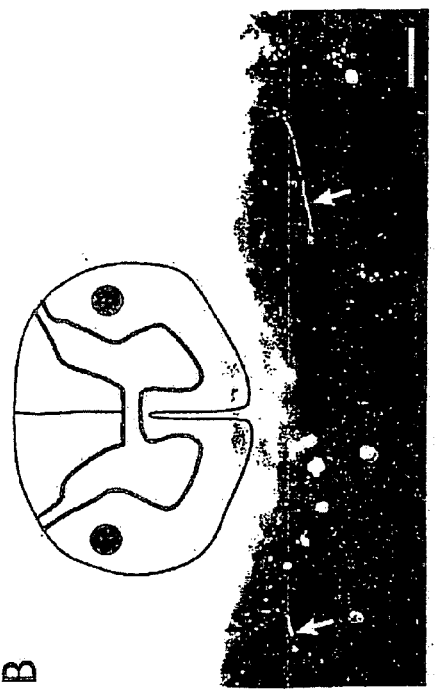
FIG. 9A to 9D Expression of neurofilament proteins and extension of neurofilament-positive neurites from human spinal cord embryonal bodies on white matter of the adult human spinal cord after 10 days in vitro. 9A: Control cultures with no KDI peptide-added; 9B: Higher magnification photograph of the same embryonal body as in 9A. The schematic drawing of the experimental situation indicates where on coronally cut sections of adult human spinal cord the embryonal bodies were placed; 9C: 5-10 μg/ml of the KDI peptide added; 9D: Higher magnification of the embryonal body of 9C.
Figure 9B:
Figure 9C:
Figure 9D:

FIG. 7 shows mean numbers of embryonal bodies (EBS; open columns) and EBS extending long neurites (black columns) on white matter of cryostat sections of the adult human spinal cord. In the presence of the KDI peptide (5-10 µg/ml), embryonal bodies attached well on white matter, and long neurites (>100 µm) extended out of the embryonal bodies in immediate contact with the myelin of the white matter. Numbers of embryonal bodies attached and sending out neurites were significantly higher in the presence of KDI as compared to the control (CtR; p<0.01) or the 10 amino acid precursor peptide P1543 (p20; p<0.01). These results show that KDI peptide has advantageous effect over the P1543 decapeptide.

FIG. 8 shows the effect of the KDI peptide on numbers of long neurites extending from embryonal bodies onto white matter of the adult human spinal cord after 10 days in vitro. In the absence of KDI peptide (CtR) few neurites extended on sections of human spinal cord white matter. In the presence of 5-10 µg/ml of the KDI peptide, a large number of long neurites extended from the embryonal bodies and grew in direct contact with the white matter (p<0.0001; Mann-Whitney non-parametric test).

In FIGS. 9A to 9D expression of neurofilament proteins and extension of neurofilament-positive neurites from human spinal cord embryonal bodies on white matter of the adult human spinal cord are shown. 10 days in vitro.

(9A) In control cultures with no KDI peptide added, the embryonal bodies are able to attach on white matter of the adult human spinal cord. No neurite outgrowth onto the white matter can be seen, but neurofilament-positive fibres (arrows) circle the outer borders of the embryonal body.

(9B) Higher magnification photograph of the same embryonal body as in 9A reveals few tiny short neurites that extend out of the embryonal body.

(9C) In the presence of 5-10 µg/ml of the KDI peptide, long neurofilament-positive nerve fibres extend out of the embryonal bodies.

(9D) High magnification reveals that neurofilament-positive neurites extend directly on top of the white matter of the adult human spinal cord. Note that the cross-section of the adult human spinal cord is also neurofilament-positive.

Regeneration of Injured Spinal Cords in Rats in vivo

FIG. 10 shows stereomicroscopic images of placebo-treated (10A and 10B) and KDI peptide-treated (10C and 10D) spinal cords of adult rats three months after injury. The ventral (A, C) side of the spinal cord shows the injury site (white arrow). On the dorsal side (black arrow) of the placebo-treated spinal cord (B) the scar is far greater than on the dorsal side of the KDI-treated spinal cord (D).

Preliminary motor scores were obtained from animals treated with KDI, and from control animals. The scores given are based on walking scores, which were evaluated by a person who did not know the treatments of individual animals. The scores for each animal were calculated by adding up the walking scores obtained within a 12 week follow-up-time after the operation. The walking score consisted of evaluation of the walking of an animal on a flat surface (on a table). The scores of six animals in placebo-group and six-animals, in the KDI-group were analysed and statistically compared. The statistical evaluation of motor scores of the rats with total spinal cord transections was done using a non-parametric Mann-Whitney test using a two-tailed P-value. The P-value obtained was 0.0022, and was considered very significant. The mean motor score for the placebo group was 11±2.4 (SEM) and that of the KDI-group was 78±5.8 (SEM). The mean of the motor score of a normal non-operated animal within the same observation period would be 120.

REFERENCES

Bronfman F C, Garrido J, Alvarez A, Morgan C, Inestrosa N C. 1996. Laminin inhibits amyloid-β-peptide fibrillation. Neurosci Lett 218:201-203.

Corset V, Nguyen-Ba-Charvet K T, Forcet C, Moyse E, Chedotal A, Mehlen P. 2000. Netrin-1-mediated axon outgrowth and cAMP production requires interaction with adenosine A2b receptor. Nature 407:747-750.

Drouet B, Pincon-Raymond M, Chambaz J, Pillot T. 1999. Laminin-1 attenuates beta-amyloid peptide (1-40) neurotoxicity of cultured fetal rat cortical neurons. J Neurochem. 73:742-749.

Hager G, Pawelzik H, Kreutzberg G W and Zieglgänsberger W. 1998. A peptide derived from a neurite outgrowth-promoting domain of the γ1 chain of laminin modulates the electrical properties of neocortical neurons. Neuroscience 86:1145-1154.

Hille B. 1992. Ionic channels of excitable membranes. Sunderland, Mass.: Sinauer Associates, Inc. p. 1-607.

Liesi P, Närvänen A, Soos J, Sariola H, Snounou G. 1989. Identification of a neurite outgrowth-promoting domain of laminin using synthetic peptides. FEBS Lett 224:141-148.

Liesi P. 1990. Extracellular matrix and neuronal movement. Experientia 46:900-907.

Liesi P, Hager G, Dodt H-U, Seppälä I J, Zieglgänsberger W. 1995. Domain specific antibodies against a neurite outgrowth domain of the B2 chain of laminin inhibit neuronal migration in neonatal rat cerebellum. J Neurosci Res 40:199-206.

Liesi P, Wright J M. 1996. Weaver granule neurons are rescued by calcium channel antagonists and antibodies against a neurite outgrowth domain of B2 chain of laminin. J Cell Biol 134:447-486.

Liesi P, Fried G, Stewart R. 2001. Neurons and glial cells of the embryonic human brain and spinal cord express multiple and distinct isoforms of laminin; J Neurosci Res 64:144-167.

Matsuzawa M, Weight F, Potember R, Liesi P. 1996a. Directional neurite outgrowth and axonal differentiation of embryonic hippocampal neurons are induced by a neurite outgrowth domain of the B2 chain of laminin. Int J Dev Neurosci 14:283-295.

Matsuzawa M, Liesi P, Knoll W. 1996b. Chemically modifying glass surfaces to study substratum-guided neurite outgrowth in culture. J Neurosci Meth 69:189-196.

Matsuzawa, M., Tokomitsu, S., Knoll, W. and Liesi, P. 1998. A molecular gradient along the axon pathway is not required for axon guidance. J. Neurosci. Res. 53:114-124.

Meyerhardt J A, Caca K, Eckstrand B C, Hu G, Lengauer C, Banavali S, Look A T, Fearon E R. 1999. Netrin-1: interaction with deleted in colorectal cancer (DCC) and alterations in brain tumors and neuroblastomas. Cell Growth Differ 10:35-42.

Murtomäki S, Risteli L, Risteli J, Johansson S Koivisto U-M, Liesi P. 1992. Laminin and its neurite outgrowth promoting domain associate with the Alzheimer and Down syndrome brains. J Neurosci Res 32:261-273.

Murtomäki S, Trenkner E, Wright J M, Saksela O, Liesi P. 1995. Increased proteolytic activity of the weaver granule neurons may participate in neuronal death in cerebellum of the weaver mutant mouse. Dev Biol 168:635-648.

Nakagami Y, Abe K, Nishiyama N, Matsuki N. 2000. Laminin degradation by plasmin regulates long-term potentiation. J Neurosci 20:2003-2010.

Nomizu M, Kim W H, Yamamura K, Utani A, Song S-Y, Otaka A, Roller P P, Kleinman H and Yamada Y. 1995. Identification of cell binding sites in the laminin □1 chain carboxyl-terminal globular domain by systematic screening of synthetic peptides. J. Biol. Chem. 270:20583-20590.

Seil F. 1998. The extracellular matrix molecule, laminin, induces Purkinje cell dendritic spine proliferation in granule cell depleted cerebellar cultures. Brain Res 795:112-120.

Serafini T, Kennedy T E, Galko M J, Mirzayan C, Jessell T M, Tessier-Lavigne M. 1994. The netrins define a family of axon outgrowth-promoting proteins homologous to C. elegans UNC-6. Cell 78:409-424.

Utani A, Nomizu M, Timpl R, Roller P P and Yamada Y. 1994. Laminin chain assembly. Specific sequences at the C-terminus of the long arm are required for the formation of specific double- and triple-stranded coiled-coil structures. J. Biol. Chem. 269:19167-19175.

The invention claimed is:

1. A method of treating spinal cord injury, which comprises:
   administering to a subject in need thereof an effective amount of the biologically active tripeptide KDI, thereby treating spinal cord tissue by regenerating injured or degenerating spinal cord tissue.

2. The method according to claim 1, wherein administering the biologically active KDI tripeptide comprises administering the biologically active tripeptide with a mini pump system directly to an area of the spinal cord that has been subject to trauma.

3. The method according to claim 1, wherein administering the biologically active KDI tripeptide comprises injecting the biologically active KDI tripeptide into the epidural space.

* * * * *